United States Patent
Smith

(10) Patent No.: US 10,052,480 B2
(45) Date of Patent: Aug. 21, 2018

(54) FITTING BILATERAL HEARING PROSTHESES

(71) Applicant: Cochlear Limited, Macquarie University (AU)

(72) Inventor: Zachary M. Smith, Greenwood Village, CO (US)

(73) Assignee: Cochlear Limited, Macquarie University (AU)

( * ) Notice: Subject to any disclaimer, the term of this patent is extended or adjusted under 35 U.S.C. 154(b) by 0 days.

(21) Appl. No.: 15/461,721

(22) Filed: Mar. 17, 2017

(65) Prior Publication Data
US 2017/0189680 A1     Jul. 6, 2017

Related U.S. Application Data

(60) Continuation of application No. 14/967,701, filed on Dec. 14, 2015, now Pat. No. 9,630,009, which is a (Continued)

(51) Int. Cl.
*A61N 1/36*     (2006.01)
*H04R 25/00*     (2006.01)
*A61N 1/05*     (2006.01)

(52) U.S. Cl.
CPC ....... *A61N 1/36032* (2013.01); *A61N 1/0541* (2013.01); *A61N 1/36036* (2017.08); (Continued)

(58) Field of Classification Search
CPC ............ A61N 1/36032; A61N 1/36036; A61N 1/0541; H04R 25/552; H04R 25/606; H04R 25/70
See application file for complete search history.

(56) References Cited

U.S. PATENT DOCUMENTS

| | | |
|---|---|---|
| 5,434,924 A | 7/1995 | Jampolsky |
| 5,870,481 A | 2/1999 | Dymond et al. |

(Continued)

FOREIGN PATENT DOCUMENTS

| | | |
|---|---|---|
| JP | 09284898 A | 10/1997 |
| KR | 1020060072555 A | 6/2006 |

OTHER PUBLICATIONS

International Search Report and Written Opinion in counterpart International Application No. PCT/IB2013/056007, dated Feb. 26, 2014.

(Continued)

*Primary Examiner* — Catherine Voorhees
(74) *Attorney, Agent, or Firm* — Edell, Shapiro & Finnan, LLC

(57) ABSTRACT

Disclosed herein are methods, systems, and computing devices for fitting bilateral hearing prostheses. An example method includes sending a signal to a first hearing prosthesis and a second hearing prosthesis. The signal causes the first hearing prosthesis to deliver a first stimulus to a body part in a left auditory pathway of a user. The signal also causes the second hearing prosthesis to deliver a second stimulus to a body part in a right auditory pathway of the user. The first stimulus and the second stimulus cause the user to perceive a sound and are delivered simultaneously. The method also includes receiving an indication of a perception of the sound by the user. The method further includes determining an adjustment to at least one of the first stimulus or the second stimulus based on the perception of the sound by the user.

19 Claims, 10 Drawing Sheets

Related U.S. Application Data continuation of application No. 14/097,470, filed on Dec. 5, 2013, now Pat. No. 9,232,327, which is a division of application No. 13/585,596, filed on Aug. 14, 2012.

(52) U.S. Cl.
CPC ......... *H04R 25/552* (2013.01); *H04R 25/606* (2013.01); *H04R 25/70* (2013.01)

(56) References Cited

U.S. PATENT DOCUMENTS

| | | |
|---|---|---|
| 6,010,532 A | 1/2000 | Kroll et al. |
| 6,449,372 B1 | 9/2002 | Greminger |
| 6,496,734 B1 | 12/2002 | Money |
| 7,043,303 B1 | 5/2006 | Overstreet |
| 7,136,706 B1 * | 11/2006 | Voelkel .............. A61N 1/36036 607/55 |
| 9,232,327 B2 | 1/2016 | Smith |
| 2001/0014818 A1 | 8/2001 | Kennedy |
| 2006/0100672 A1 | 5/2006 | Litvak |
| 2007/0135862 A1 | 6/2007 | Nicolai et al. |
| 2008/0300653 A1 | 12/2008 | Svirsky |
| 2009/0030484 A1 | 1/2009 | Chambers |
| 2010/0198301 A1 | 8/2010 | Smith |
| 2010/0310101 A1 | 12/2010 | Anderson |
| 2011/0019846 A1 * | 1/2011 | Anderson .............. A61B 5/121 381/313 |
| 2011/0257704 A1 | 10/2011 | Kals et al. |
| 2012/0116480 A1 | 5/2012 | Tsay et al. |
| 2012/0232616 A1 | 9/2012 | Van Baelen et al. |

OTHER PUBLICATIONS

Extended European Search Report dated Apr. 7, 2016 in corresponding EP Application No. 13829485.5-166/2885928.

\* cited by examiner

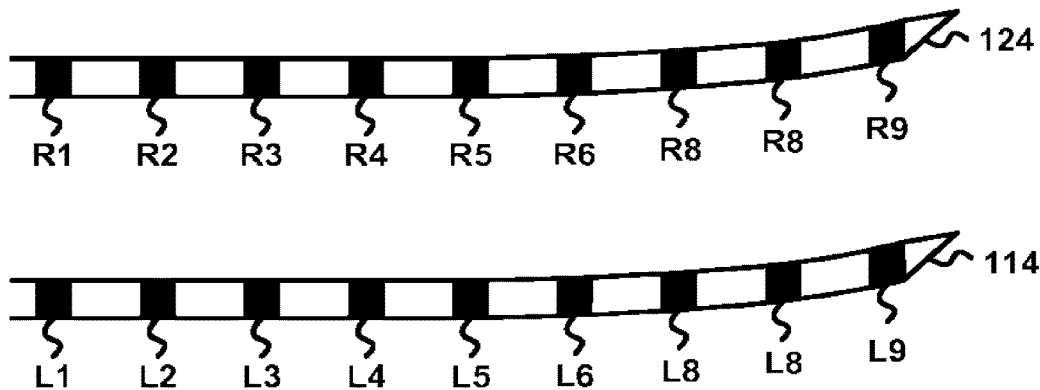
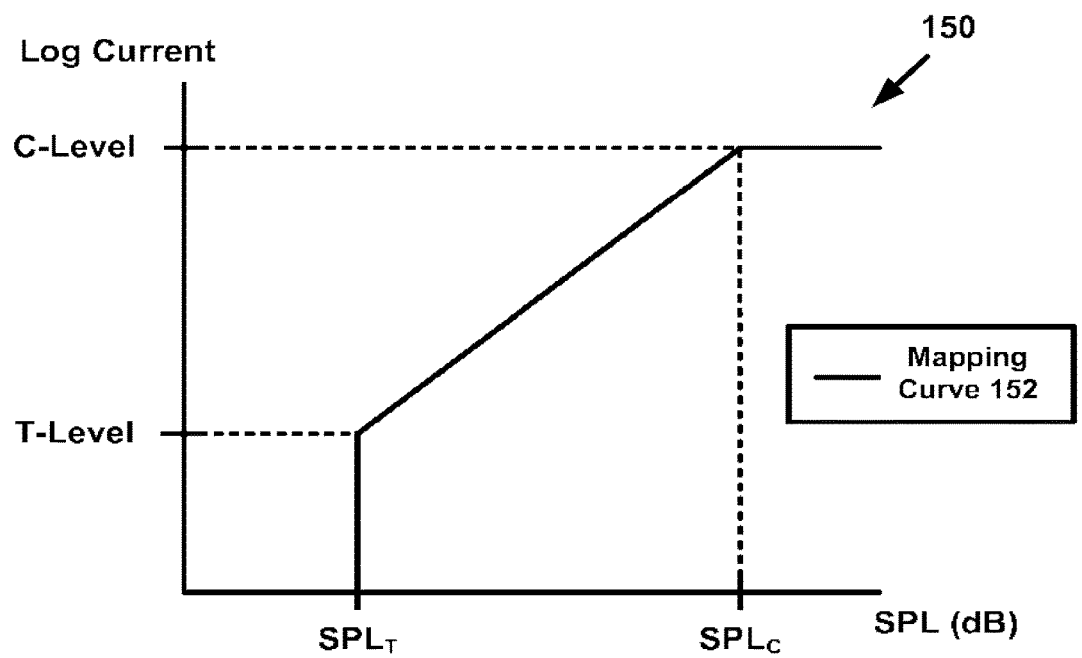
FIG.1B
FIG. 1C

FITTING BILATERAL HEARING PROSTHESES

CROSS-REFERENCE TO RELATED APPLICATIONS

This application is a continuation of U.S. patent application Ser. No. 14/967,701, filed Dec. 14, 2015, which is a continuation of U.S. patent application Ser. No. 14/097,470, filed Dec. 5, 2013, now U.S. Pat. No. 9,232,327, which in turn is a divisional of U.S. patent application Ser. No. 13/585,596, filed Aug. 14, 2012. The entirety of each of these applications is incorporated herein by reference.

BACKGROUND

Due to hearing loss, some individuals have difficulty perceiving or are unable to perceive sound. In order to perceive at least a portion of a sound, these individuals may benefit from the use of a hearing prosthesis. Certain hearing prostheses are designed to assist users having specific types of hearing loss. In a bilateral hearing prosthesis system, a user employs a first hearing prosthesis for the user's left ear and a second hearing prosthesis for the user's right ear.

The effectiveness of the hearing prostheses depends on the type and severity of a user's hearing loss. Furthermore, depending on the hearing prostheses, the user may perceive sound as a person with normal hearing, or the hearing prostheses may allow the user to perceive a portion of the sound. The effectiveness of the hearing prostheses also depends on how well the prostheses are configured for, or "fitted" to, a user of the hearing prosthesis. Fitting the hearing prostheses, sometimes also referred to as "programming," "calibrating," or "mapping," creates a set of control settings and other data that define the specific characteristics of the stimuli (in the form of acoustic, mechanical, or electrical signals) delivered to the relevant portions of the person's outer ear, middle ear, inner ear, auditory nerve, or other body part. The control settings are based on the user's type and severity of hearing loss. This configuration information is sometimes referred to as the user's "program" or "map."

SUMMARY

A first method for fitting bilateral hearing prostheses is provided. The first method includes sending a signal to a first hearing prosthesis and a second hearing prosthesis. The signal causes the first hearing prosthesis to deliver a first stimulus to a body part in a left auditory pathway of a user. The signal also causes the second hearing prosthesis to deliver a second stimulus to a body part in a right auditory pathway of the user. The first stimulus and the second stimulus cause the user to perceive a sound and are delivered simultaneously. The first method also includes receiving an indication of a perception of the sound by the user. The first method additionally includes determining an adjustment to at least one of the first stimulus or the second stimulus based on the perception of the sound by the user.

A second method for fitting bilateral hearing prostheses is also provided. The second method includes sending a first signal to a first hearing prosthesis. The first signal includes information indicative of a first stimulus, which the first hearing prosthesis delivers to a first body part in a left auditory pathway of a user. The second method also includes sending a second signal to a second hearing prosthesis. The second signal includes information indicative of a second stimulus, which the second hearing prosthesis delivers to a second body part in a right auditory pathway of the user. The first stimulus and the second stimulus are delivered simultaneously. The second method further includes determining whether the first stimulus and the second stimulus are at a maximum level. The second method additionally includes determining that the first stimulus corresponds to a maximum sound pressure level in response to determining that the first stimulus and the second stimulus are at the maximum level. Additionally, the second method includes determining that the second stimulus corresponds to the maximum sound pressure level in response to determining that the first stimulus corresponds to the maximum sound pressure level. The maximum sound pressure level is a sound pressure level of a sound above which the sound is saturated.

A third method for fitting bilateral hearing prostheses is also provided. The third method includes performing a sweep of electrode arrays included in bilateral hearing prostheses. Performing the sweep includes causing a first interaural electrode pair to deliver a first stimulation to a user of the bilateral hearing prostheses so that the user perceives a first sound. Performing the sweep also includes causing a second interaural electrode pair to deliver a second stimulation to the user so that the user perceives a second sound. The second stimulation is delivered after the first stimulation. The third method also includes receiving an input signal that includes information indicative of a difference between the first sound and the second sound as perceived by the user. The third method further includes determining an adjustment to a stimulus current of an electrode included in one of the first interaural electrode pair or the second interaural electrode pair. The adjustment is based on the input signal. Additionally, the stimulus current is a component of one of the first stimulation or the second stimulation. The third method also includes applying the adjustment to a mapping curve of the electrode. The mapping curve includes information indicative of a plurality of stimulus currents corresponding to a plurality of sound pressure levels.

A system for fitting bilateral hearing prostheses is also provided. The system includes a first cochlear implant and a second cochlear implant. The first cochlear implant includes a first electrode array that is implanted in a left cochlea of a user, and the second cochlear implant includes a second electrode array that is implanted in a right cochlea of the user. The system also includes a computing device connected to the first cochlear implant and the second cochlear implant. The computing device is configured to fit the first cochlear implant and the second cochlear implant to the user by sending a test signal to the first cochlear implant and the second cochlear implant. The test signal causes an interaural electrode pair to stimulate the left cochlea and the right cochlea of the user so that the user perceives a sound. The interaural electrode pair includes a first electrode included on the first electrode array. The interaural electrode pair also includes a second electrode included on the second electrode array. Additionally, the test signal includes information indicative of a first stimulus current for the first electrode and a second stimulus current for the second electrode. The computing device is also configured to fit the first cochlear implant and the second cochlear implant to the user by determining whether an input signal received at a user interface includes information indicative of a request to adjust the sound. In response to determining that the input signal includes information indicative of the request, the computing device is further configured to fit the first cochlear implant and the second cochlear implant to the user by adjusting at least one of the first stimulus current or the second stimulus current based on the input signal.

Additionally, a computing device is provided. The computing device includes a user interface configured to receive an indication of an adjustment to a first stimulus and a second stimulus delivered to a user of a first hearing prosthesis and a second hearing prosthesis. The computing device also includes an interface module configured to connect the computing device to the first hearing prosthesis and the second hearing prosthesis. The computing device additionally includes a processor. The processor is configured to receive an input signal from the user interface that includes information indicative of an adjustment to the first stimulus and the second stimulus. The computing device is also configured to modify the first stimulus and the second stimulus based on the adjustment. The computing device is further configured to send a first signal to the first hearing prosthesis and a second signal to the second hearing prosthesis. The first signal includes information indicative of a modified first stimulus. The second signal includes information indicative of a modified second stimulus. The first signal causes the first hearing prosthesis to deliver the modified first stimulus to the user at about a same time as the second signal causes the second hearing prosthesis to deliver the modified second stimulus to the user.

These as well as other aspects and advantages will become apparent to those of ordinary skill in the art by reading the following detailed description, with reference where appropriate to the accompanying drawings. Further, it is understood that this summary is merely an example and is not intended to limit the scope of the invention as claimed.

BRIEF DESCRIPTION OF THE FIGURES

Presently preferred embodiments are described below in conjunction with the appended drawing figures, wherein like reference numerals refer to like elements in the various figures, and wherein:

FIG. 1B illustrates electrode arrays depicted in FIG. 1A, according to an example;

FIG. 1C is a graph of a mapping curve of an electrode depicted in FIG. 1B, according to an example;

DETAILED DESCRIPTION

The following detailed description describes various features, functions, and attributes of the disclosed systems, methods, and devices with reference to the accompanying figures. In the figures, similar symbols typically identify similar components, unless context dictates otherwise. The illustrative embodiments described herein are not meant to be limiting. Certain aspects of the disclosed systems, methods, and devices can be arranged and combined in a wide variety of different configurations, all of which are contemplated herein.

1. EXAMPLE SYSTEM FOR FITTING BILATERAL HEARING PROSTHESES

Figure 1A:
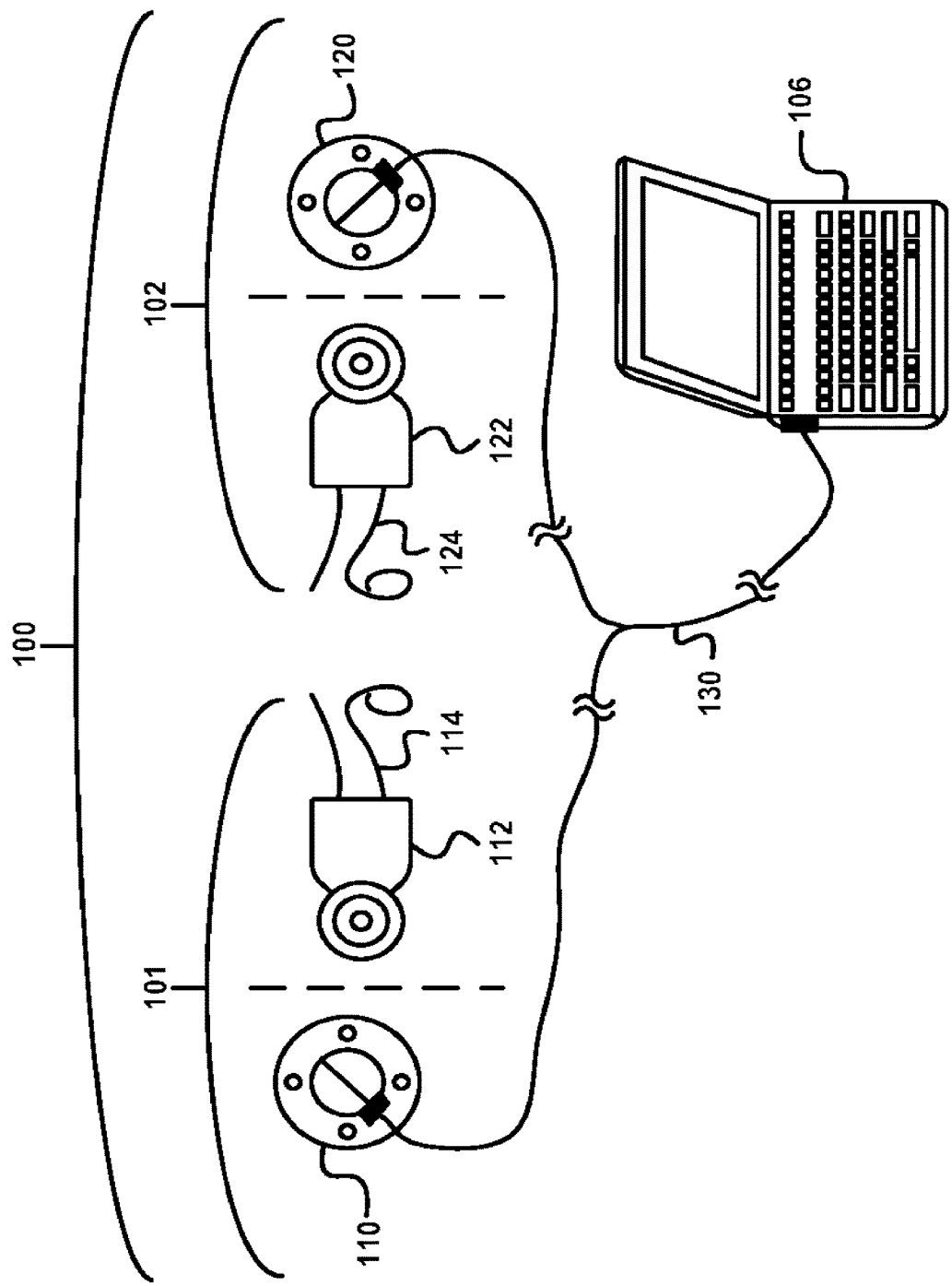
FIG. 1A illustrates components of a fitting system used for fitting bilateral hearing prostheses, according to an example.

FIG. 1A illustrates a fitting system 100 configured to fit bilateral hearing prostheses to a user. The fitting system 100 includes a first hearing prosthesis 101 and a second hearing prosthesis 102. The hearing prostheses 101, 102 are illustrated as partially implantable cochlear implants. In another example, the fitting system 100 includes other hearing prostheses, such as totally implantable cochlear implants, bone conduction devices, direct acoustic stimulation devices, auditory brain stem implants, middle ear implants, and/or any other hearing prostheses or combination of hearing prostheses suitable for use as bilateral hearing prostheses. The first hearing prosthesis 101 includes a first processing unit 110 and a first implanted unit 112, and the second hearing prosthesis 102 includes a second processing unit 120 and a second implanted unit 122. The implanted units 112, 122 are implanted in a portion of a skull of the user. In an example in which the hearing prostheses 101, 102 are totally implantable hearing prostheses, the processing units 110, 120 are also implanted in the user's skull. Additionally, a first enclosure may include the first processing units 110 and the first implanted unit 112, and a second enclosure may include the second processing unit 120 and the second implanted unit 122.

The implanted unit 112 includes a first electrode array 114, and the second implanted unit 122 includes a second electrode array 124. The first electrode array 114 is implanted in the user's left cochlea, and the second electrode array 124 is implanted in the user's right cochlea. Each electrode on the electrode array 114, 124 stimulates a portion of one of the user's cochlea that allows the user to perceive sound having a range of frequencies. The electrodes in the electrode arrays 114, 124 deliver electrical stimuli to one or more portions of the user's cochlea to allow the user to perceive at least a portion of a sound.

FIG. 1B illustrates the first electrode array 114 and the second electrode array 124. The first electrode array 114 and the second electrode array 124 are implanted in the user's left and right cochlea, respectively. To facilitate implantation, the electrodes arrays 114, 124 are made of flexible material suitable for being implanted in the user's cochlea.

The first electrode array 114 includes electrodes L1-L9, and the second electrode array 124 includes electrodes R1-R9. In one example, the electrode arrays 114, 124 may include more or fewer electrodes. For instance, the electrode arrays 114, 124 may each include twenty-two electrodes. The electrode arrays 114, 124 are implanted such that an interaural electrode pair—which is defined as one or more electrodes on the first electrode array 114 that are paired to one or more electrodes on the second electrode array 124—stimulates similar regions of the user's cochlea. In one example, corresponding electrodes on the electrode arrays 114, 124 stimulates similar regions of the user's left and right cochlea and make up an interaural electrode pair. For instance, L1 and R1 make up one interaural electrode pair. In another example, the electrode arrays 114, 124 are not implanted in the user's cochlea such that corresponding electrodes on the electrode arrays 114, 124 make up an interaural electrode pair. In this example, electrodes L1 and R3 make up an interaural electrode pair and stimulate similar regions of the user's left and right cochlea, respectively.

A loudness of the sound perceived by the user of the hearing prostheses 101, 102 depends on stimulus currents of the electrical stimuli each electrode delivers to the user in response to the processing units 110, 120 processing a sound. In general, as the stimulus current increases, the loudness of the sound perceived by the user increases. A value of a given stimulus current depends on a sound pressure level (SPL) of a sound received by one of the processing units 110, 120.

FIG. 1C is a graph 150 of a mapping curve 152 of one of the electrodes included on one of the electrode arrays 114, 124. The mapping curve 152 is plotted on a log-log scale, with the x-axis representing the SPL of a sound in decibels, and the y-axis representing a logarithm of the stimulus current. The stimulus current is expressed in any unit suitable for use in the hearing prostheses 101, 102. In one example, the unit is microamperes. In another example, the unit is any unit capable of being converted to microamperes. For illustrative purposes, the mapping curve 152 corresponds to the electrode L1.

The electrical dynamic range for the electrode L1 is a difference between a threshold level (T-Level) and a maximum comfort level (C-Level). The T-Level for the electrode L1 corresponds to a stimulus current that results in the user just being able to hear a sound at a given frequency. In other words, the T-Level is the stimulus current below which the user is not able to perceive the sound. The C-Level for the electrode L1 corresponds to the stimulus current applied by the electrode to the user's cochlea that results in a maximum loudness of the sound at a given frequency that the user can perceive comfortably. That is, the C-Level is the stimulus current above which the user perceives the sound as being painful or uncomfortably loud.

The SPL of the sound at the T-Level is identified as $SPL_T$, and the SPL of the sound at the C-Level is identified as SPLc. $SPL_T$ and $SPL_c$ are fixed. In one example, the values of $SPL_T$ and SPLc depend on operating characteristics of the components of the hearing prosthesis 101. In another example, the values of $SPL_T$ and SPLc depend on the severity of the user's hearing loss at a frequency range corresponding to the electrode. A sound having an SPL less than the $SPL_T$ is typically discarded by the processing unit 110 and does not result in stimulation. For a sound having an SPL that is between the $SPL_T$ and the SPLc, the stimulus current varies approximately logarithmically with the SPL of the sound, resulting in the mapping curve 152 being approximately linear on the graph 150 between $SPL_T$ and SPLc. For a sound having an SPL greater than SPLc, the stimulus current is fixed at the C-Level. In other words, SPLc is the saturation level for the electrode.

Each of the electrodes L1-L9, R1-R9 has a mapping curve. While users of the hearing prostheses 101, 102 may have a similar type of hearing loss (e.g., sensorineural hearing loss), each user may have a unique sensitivity to stimulation by different electrodes. To accommodate the user's specific hearing loss, the hearing prostheses 101, 102 are fit to the user of the hearing prostheses 101, 102 using a computing device 106. Fitting the hearing prostheses 101, 102 to the user includes determining the T-Level and the C-Level for each of the electrodes L1-L9 and R1-R9. A cable 130 is shown as connecting the computing device 106 to each of the processing units 110, 120 via a cable 130. In another example, the computing device 106 is wirelessly connected to the processing units 110, 120.

To determine the T-Level and/or the C-Level for an electrode on one of the electrode arrays 114, 124, the computing device 106 sends a test signal to at least one of the processing units 110, 120. The test signal includes information indicative of a stimulus that one or more of the electrodes L1-L9, R1-R9 should deliver to the user. The test signal also indicates a duration of each stimulus, such as a duration of about 500 msec. In one example, the user can increase or decrease the duration of the stimulus. The processing units 110, 120 determine a stimulation signal(s) based on the test signal, and send a stimulation signal(s) to the implanted units 112, 122, respectively. Depending on the application, the implanted units 112, 122 use the stimulation signal(s) to cause one or more electrodes on the electrode arrays 114, 124 to stimulate at least one of the user's cochlea.

Figure 5A:
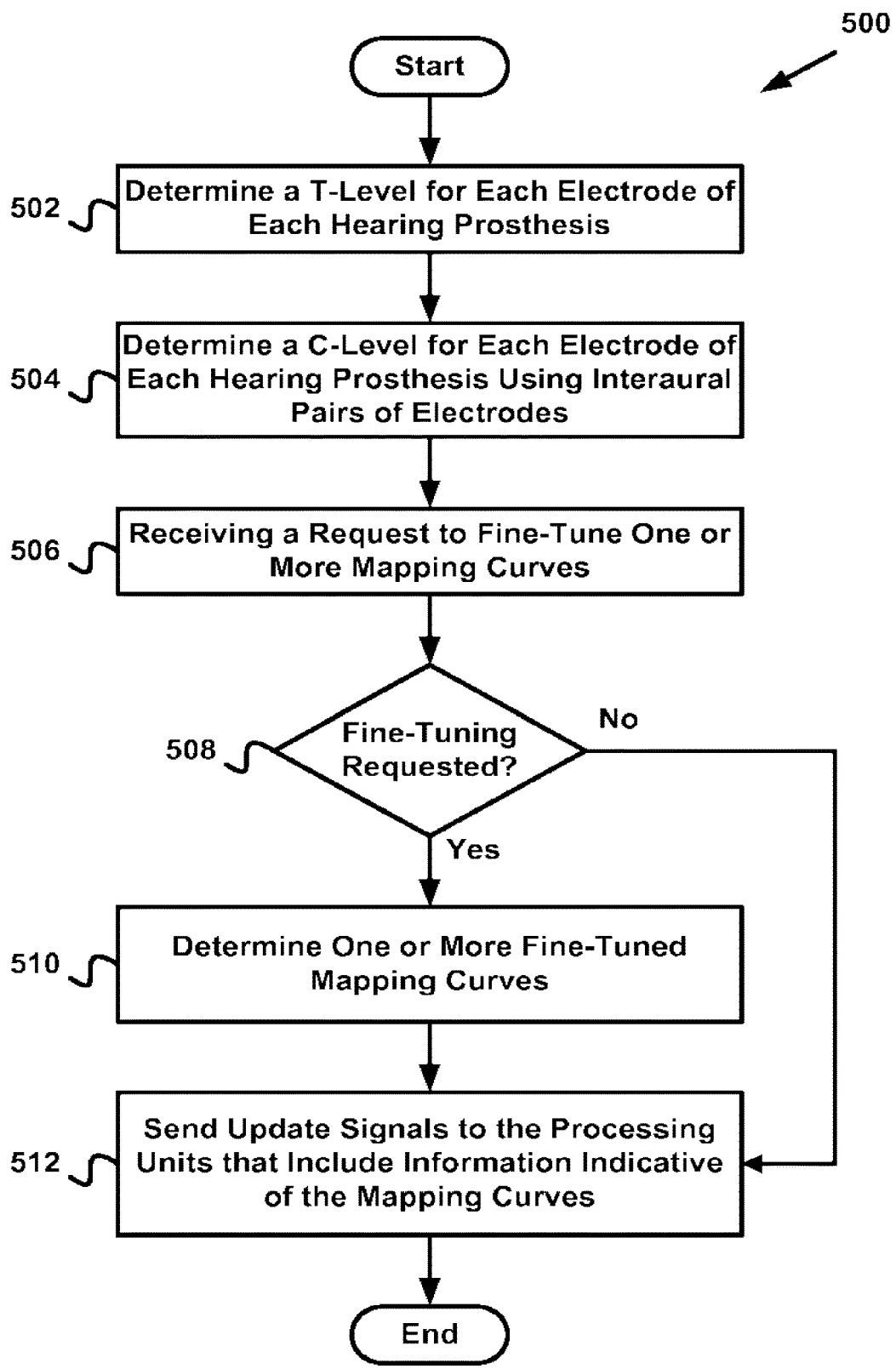
FIG. 5A is a flow diagram of a method for fitting hearing prostheses in a bilateral hearing prosthesis system, according to an example.
Figure 6:
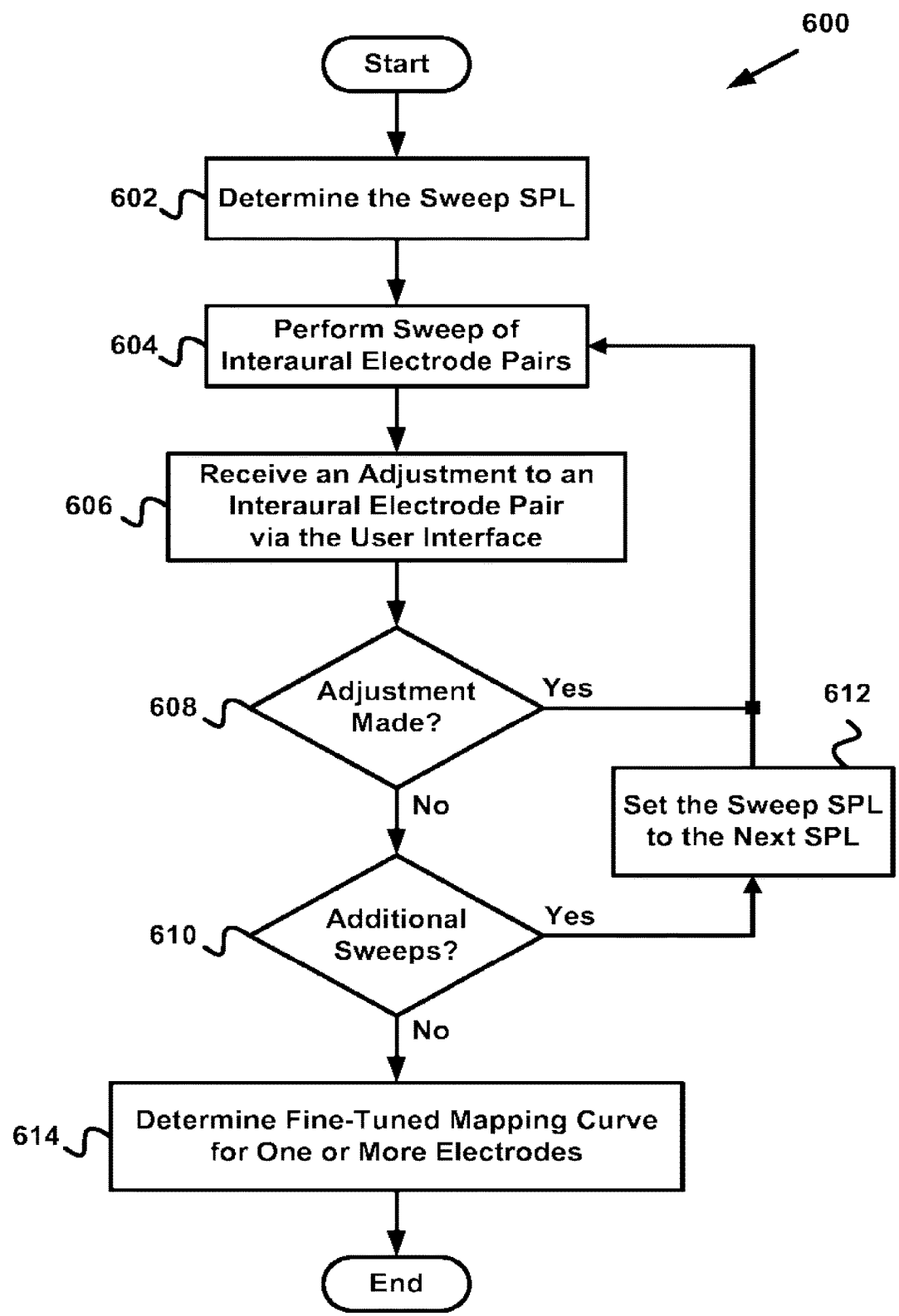
FIG. 6 is a flow diagram of a method for determining currents for interaural pairs of electrodes, according to an example.

Example methods for fitting the hearing prostheses 101, 102 are described in more detail with respect to FIGS. 5A and 6.

2. EXAMPLE COMPONENTS OF A SYSTEM FOR FITTING BILATERAL HEARING PROSTHESES

Figure 2:
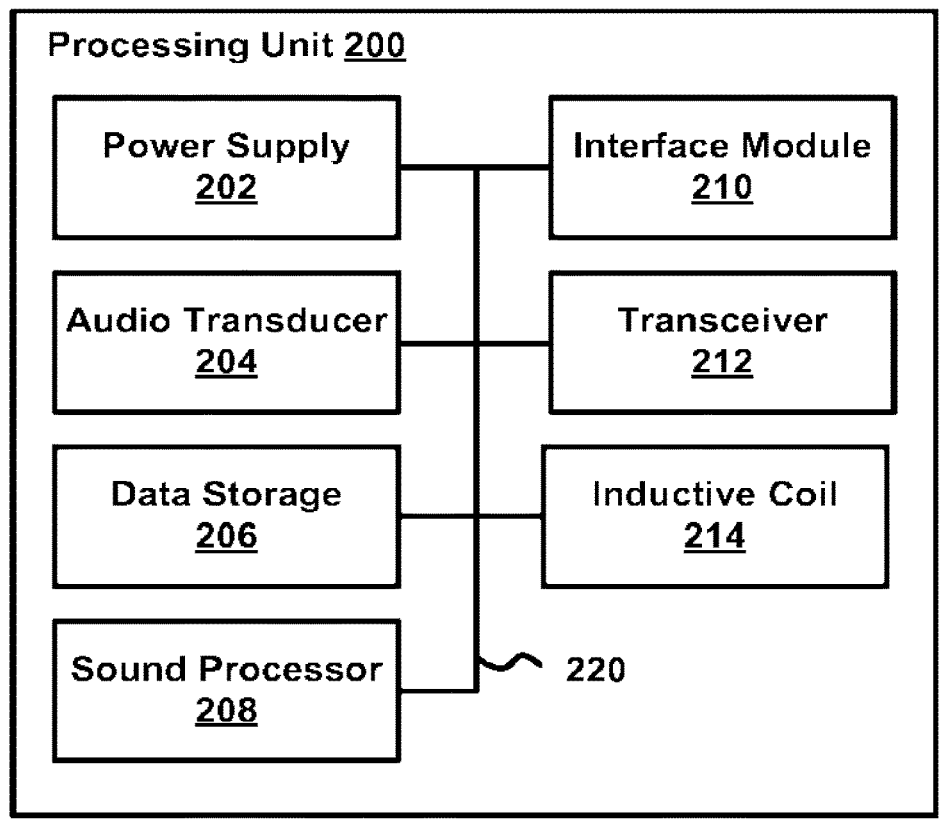
FIG. 2 is a block diagram of a processing unit depicted in FIG. 1A, according to an example.

FIG. 2 is a block diagram of a processing unit 200 of a hearing prosthesis. The processing unit 200 is one example of the processing units 110, 120 depicted in FIG. 1A. The processing unit 200 includes a power supply 202, an audio transducer 204, a data storage 206, a sound processor 208, an interface module 210, a transceiver 212, and an inductive coil 214, all of which may be connected directly or indirectly via circuitry 220. For illustrative purposes, the processing unit 200 is the processing unit 110 depicted in FIG. 1A.

The power supply 202 supplies power to various components of the processing unit 200 and can be any suitable power supply, such as a rechargeable or a non-rechargeable battery. In one example, the power supply 202 is a battery that can be charged wirelessly, such as through inductive charging. In another example, the power supply 202 is not a replaceable or rechargeable battery and is configured to provide power to the components of the processing unit 200 for the operational lifespan of the processing unit 200. The power supply 202 also provides power to the implanted unit of the hearing prosthesis, such as one of the implanted units 112, 122 described with respect to FIG. 1 via the inductive coil 214.

The audio transducer 204 receives a sound from an environment and sends a sound signal to the sound processor 208. In one example, the processing unit 200 is a bone conduction device, and the audio transducer 204 is an omnidirectional microphone. In another example, the processing unit 200 is a cochlear implant, an auditory brain stem implant, a direct acoustic stimulation device, a middle ear implant, or any other hearing prosthesis now known or later developed that is suitable for assisting a user of the hearing prosthesis 101 in perceiving sound. In this example, the audio transducer 204 is an omnidirectional microphone, a directional microphone, an electro-mechanical transducer, or any other audio transducer now known or later developed suitable for use in the type of hearing prosthesis employed. Furthermore, in other examples the audio transducer 204 includes one or more additional audio transducers.

The data storage 206 includes any type of non-transitory, tangible, computer readable media now known or later developed configurable to store program code for execution by a component of the processing unit 200 and/or other data associated with the processing unit 200. The data storage 206 also stores information indicative of a mapping curve for the electrodes L1-L9 of the electrode array 114. The data storage 206 may also store computer programs executable by the sound processor 208.

The sound processor 208 is configured to determine a stimulation signal suitable for use by the implanted unit of the hearing prosthesis. In one example, the sound processor 208 is a digital signal processor. In another example, the sound processor 208 is any processor or combination of processors now known or later developed suitable for use in a hearing prosthesis. Additionally, the sound processor 208 may include additional hardware for processing the audio signal, such as an analog-to-digital converter and/or one or more filters.

The stimulation signal includes information indicative of a stimulus current for one or more of the electrodes L1-L9. In one example, the sound processor 208 determines the stimulation signal by processing the sound signal received from the audio transducer 204. In another example, such as during a fitting process, the sound processor 208 receives a signal from the computing device 106 that includes information indicative of the stimulus current for one or more of the electrodes L1-L9. Alternatively, the sound processor 208 receives the sound signal from the computing device 106.

The sound processor 208 also receives an update signal from the computing device via the interface module 210. Once fitting is completed, the computing device 106 sends the update signal to processing unit 200 via the cable 130. The update signal includes information indicative of the mapping curves for one or more of the electrodes L1-L9 as determined by the computing device 106. The sound processor 208 stores the information included in the update signal in the data storage 206.

The interface module 210 is configured to receive the test signal and/or the update signal from the computing device 106. The interface module 210 includes a component suitable for receiving signals from the computing device 106 via a wired and/or a wireless connection. Upon receiving a signal from the computing device 106, the interface module 210 sends the signal to the sound processor 208. In another example, the interface module 210 is configured to store the information included in the update signal in the data storage 206.

The transceiver 212 receives the stimulation signal from the sound processor 208 and modulates the stimulation signal to form a transmission signal. The transmission signal also includes the power signal received from the power supply 202. In one example, the transceiver 212 modulates the stimulation signal using a time-division multiple-access modulation scheme. In another example, the transceiver 212 uses any modulation scheme now known or later developed suitable for inductively transmitting the stimulation signal to an implanted unit of a hearing prosthesis. The transceiver 212 sends the transmission signal to the inductive coil 214.

The inductive coil 214 receives the transmission signal from the transceiver 212 and inductively transmits the transmission signal to the implanted unit 112. The inductive coil 214 is constructed of any material or combination of materials suitable for inductively transferring a power signal to the implanted unit.

Figure 3:
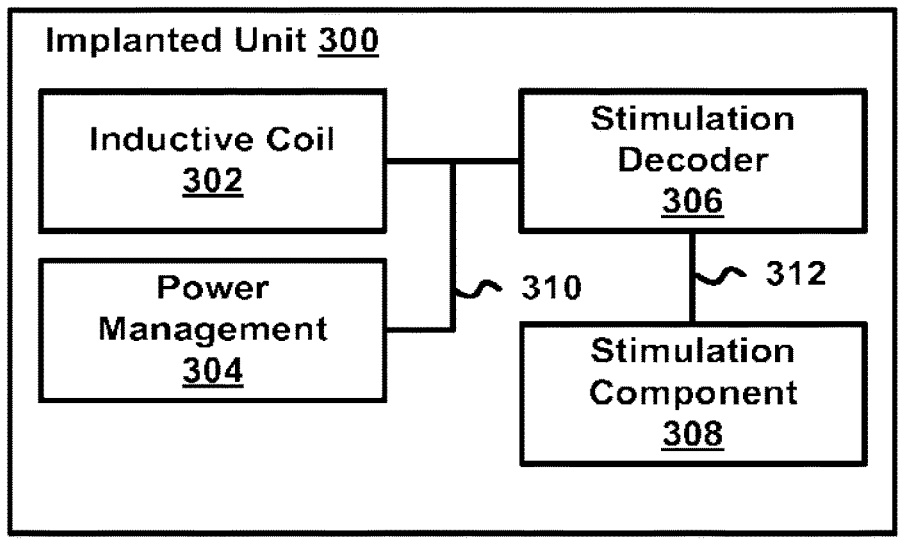
FIG. 3 is a block diagram of an implanted unit depicted in FIG. 1A, according to an example.

FIG. 3 is a block diagram of an implanted unit 300 of a hearing prosthesis. The implanted unit 300 is one example of the implanted units 112, 124 depicted in FIG. 1A. The implanted unit 300 includes an inductive coil 302, power management 304, and a stimulation decoder 306, all of which are connected directly or indirectly via circuitry 310. The implanted unit 300 also includes a stimulation component 310 that is connected to the stimulation decoder 306 via circuitry 312. For illustrative purposes, the implanted unit 300 is the implanted unit 112 depicted in FIG. 1A.

The inductive coil 302 receives the transmission signal from the processing unit 110. The inductive coil 302 is constructed of any biocompatible material or combination of materials suitable for inductively receiving power from the processing unit 110. The inductive coil 302 transfers the power signal to the power management 304. Alternatively, the implanted unit 304 may not include the power management 304. In this case, the inductive coil 302 transfers the power signal to the stimulation decoder 306 and the stimulation component 308.

The power management 304 receives the transmission signal from the inductive coil 302 and distributes power to the components of the implanted unit 300. The power management 304 also includes a component suitable for removing the coded stimulation signal from the power signal. The power management 304 sends the coded stimulation signal to the stimulation decoder 306. The stimulation decoder 306 decodes the coded stimulation signal and transfers the stimulation signal to the stimulation component 308.

The stimulation component 308 receives the stimulation signal from the stimulation decoder 306 and generates a stimulus based on the stimulation signal. In one example, the stimulation component 308 includes a first subcomponent configured to generate the stimulus and a second subcomponent configured to deliver the stimulus to an auditory organ, such as a cochlea, an auditory nerve, a brain, and any other organ or body part capable of assisting a user of the hearing prosthesis in perceiving at least a portion of a sound. The first subcomponent generates the stimulus based on the stimulation signal and sends the stimulus to the second component. The second subcomponent delivers the stimulus to the body part of the user.

For instance, since implanted unit 300 is part of a cochlear implant, the stimulation component 308 includes a signal generator and the electrode array 114. The signal generator generates an electrical signal based on the stimulation signal and sends the electrical signal to the electrode array 114. The electrical signal causes one or more of the electrodes L1-L9 to deliver one or more electrical stimuli to a portion of the user's left cochlea. The one or more electrical stimuli cause the left cochlea to stimulate the user's left auditory nerve, thereby allowing the user to perceive at least a portion of a sound from the user's left ear.

Figure 4A:
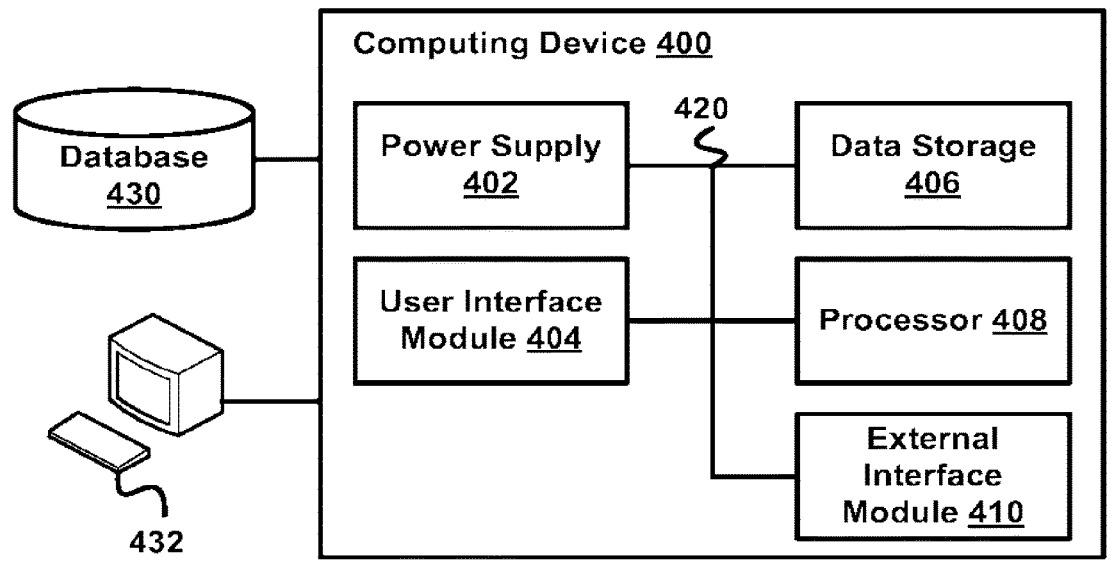
FIG. 4A is a block diagram of a computing device depicted in FIG. 1, according to an example.

FIG. 4A is a block diagram of a computing device 400. The computing device 400 is one example of the computing device 106 depicted in FIG. 1A. The computing device 400 includes a power supply 402, a user interface module 404, a data storage 406, a processor 408, and an external interface module 410, all of which are connected either directly or indirectly via circuitry 420. For illustrative purposes, the computing device 400 is the computing device 106 depicted in FIG. 1A.

The power supply 402 provides power to components of the computing device 400. In one example, the power supply 402 is connected to a mains power distribution, such as an electrical outlet that supplies 120 VAC power. The power supply 402 includes electrical equipment, such as one or more transformers, that are configured to reduce the power received from the mains power distribution to a voltage suitable for use by the component of the computing device 400. The power supply 402 also includes one or more AC-DC converters. In another example, the power supply 402 includes a rechargeable battery configured to supply power to the components of the computing device 402.

The user interface module 404 is configured to receive an input from the user of the computing device 400 and to provide an output to the user. The user interface module 404 includes at least one input component capable of receiving an input from the user, such as a keyboard, a keypad, a computer mouse, a touch screen, a track ball, a joystick, and/or any other similar device now known or later discovered. The user interface module 404 includes at least one output component capable of displaying information to the user, such as a monitor, touch screen, printer, speaker, and/or any other similar device now known or later discovered.

Figure 4B:
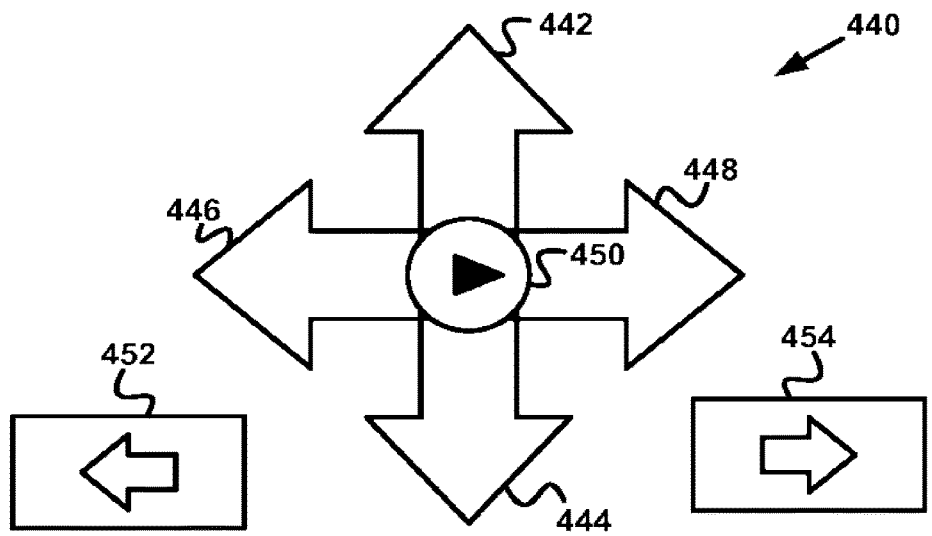
FIG. 4B illustrates an example user interface depicted in FIG. 4A, according to an example.

The user interface module 404 also includes a fitting interface configured to adjust values of stimulus currents applied by an interaural electrode pair of a hearing prosthesis. FIG. 4B illustrates an example fitting interface 440. The fitting interface 440 includes a volume increase button 442, a volume decrease button 444, a left adjust button 446, a right adjust button 448, and a play button 450. In one example, the fitting interface 440 is included as part of a physical input interface, such as a keyboard or similar device. In another example, the fitting interface 440 is displayed on an output component of a display device, such as a monitor, touch screen, or similar output component. In this example, the user interacts with fitting interface 440 using a mouse, a touch screen, or a similar input device.

During the fitting process, the user (or an audiologist or other specialist) adjusts the stimulus currents applied by one or more interaural electrode pairs. For example, consider a situation where the user is adjusting the currents applied by an interaural electrode pair that includes the electrodes L1 and R1. If the user presses the increase volume button 442, the stimulus currents of both of electrodes L1 and R1 are increased. If the user presses the decrease volume button 444, the stimulus currents of both of electrodes L1 and R1 are decreased. If the user presses the left adjust button 446, the stimulus current of the electrode L1 is increased, and/or the stimulus current of the electrode R1 is decreased. If the user presses the right adjust button 448, the stimulus current of the electrode R1 is increased, and/or the stimulus current of the electrode L1 is decreased.

In another example, the user interacts with the user interface 440 to adjust the stimulus current of one of the electrodes L1, R1 individually. For instance, pressing the left adjust button 446 increase the stimulus current of the electrode L1, and pressing the right adjust button 448 decreases the stimulus current of the electrode L1. Similarly, pressing the increase volume button 442 increase the stimulus current of the electrode R1, and pressing the volume decrease button 444 decreases the stimulus current of the electrode R1.

As an additional illustration of the operation of the fitting interface 440, consider an example in which an initial stimulus current of the electrode L1 is 150 units and an initial stimulus current of the electrode R1 is 150 units, which are represented as 150/150. In this example, interacting with one of the buttons 442-448 changes the stimulus currents of the left and right electrodes by one unit. Depressing the increase volume button 442 changes the stimulus currents to 151/151, while depressing the decrease volume button 444 changes the stimulus currents to 149/149. Similarly, depressing the left adjust button 446 changes the stimulus currents to 151/149, and depressing the right adjust button 448 changes the stimulation current to 149/151. In another example, depressing one of the buttons 442-448 changes the stimulus currents by a different amount. In yet another example, the user can determine the amount of the change in the stimulus current prior to depressing one of the buttons 442-448.

In one example, the fitting interface 440 also includes a play button 450 that allows the user to hear a sound using a present setting of the stimulus currents for the interaural electrode pair. The user is also able to cycle between interaural electrode pairs using the previous pair button 452 and the next pair button 454. In one example, an output component of the user interface module 404 provides the user with an option to select one or more interaural electrode pairs. For instance, if the user selects the interaural electrode pairs L1-R1, L2-R2, and L3-R3, interacting with one of the buttons 442-448 adjusts the stimulus current for each of the electrodes L1-L3 and R1-R3.

The data storage 406 includes any type of non-transitory, tangible, computer readable media now known or later developed configurable to store program code for execution by the computing device 400 and/or other data associated with the computing device 400. The data storage 406 stores information used by the processor 408 to fit the bilateral hearing prostheses 101, 102. The data storage 406 may also store computer programs executable by the processor 408, such as computer programs that include instructions for performing one or more steps of the methods described with respect to FIGS. 5A and 6.

The processor 408 is configured to fit the hearing prostheses 101, 102 to the user. In one example, the processor 408 executes a computer program stored in the data storage 406 to fit the hearing prostheses 101, 102. When fitting the hearing prostheses 101, 102, the processor 408 generates one or more test signals that are sent to the processing units 110, 120 via the external interface module 410. Based on inputs received via the user interface module 404, the processor 408 adjusts the stimulus currents of one or more of the electrodes L1-L9, R1-R9. Once fitting is complete, the processor 408 determines mapping curves for each of the electrodes L1-L9, R1-R9. The processor 408 then generates a first update signal that include information indicative of the mapping curves for the electrodes L1-L9, and a second update signal that includes information indicative of the mapping curves for the electrodes R1-R9. The processor 408 sends the first updates signal to the first processing unit 110 and the second update signal to the second processing unit 120 via the external interface module 410. In one example, the processor 408 also stores the mapping curves for the electrodes L1-L9, R1-R9 in the data storage 406 and/or the database 430.

The external interface module 410 connects the computing device 400 to one or more external devices, such as the hearing prostheses 101, 102, the database 430, and/or the second computing device 432. The external interface module 410 includes a component suitable for connecting the computing device 400 to the one or more external devices via a wired and/or wireless connection.

3. EXAMPLE METHODS FOR FITTING A BILATERAL HEARING PROSTHESIS

FIG. 5A is a flow diagram of a method 500 for fitting bilateral hearing prostheses. A computing device may utilize the method 500 to determine control settings for hearing prostheses. While the fitting system 100, the processing unit 200, and the computing device 400 are described for purposes of illustrating the method 500, it is understood that other devices may be used.

The method 500 and other methods and processes disclosed herein may include one or more operations, functions, or actions as illustrated in the blocks. Although the blocks are illustrated in sequential order, these blocks may be performed in parallel and/or in a different order than that described herein. Also, the various blocks may be combined into fewer blocks, divided into additional blocks, and/or removed based upon the desired implementation.

In addition, for the method 500 and other processes and methods disclosed herein, the flow diagram shows functionality and operation of one possible implementation of one example. In this regard, each block may represent a module, a segment, or a portion of program code, which includes one or more instructions executable by a process for implementing specific logical functions or steps in the process. The program code may be stored on any type of computer readable medium, such as a storage device including a disk or hard drive, for example. The computer readable medium may include non-transitory computer readable media, such as a computer readable media that stores data for a short period of time, such as register memory, processor cache, or Random Access Memory ("RAM"). The computer readable medium may also include non-transitory computer readable media suitable as secondary or persistent long term storage, such as read-only memory ("ROM"), one-time programmable memory (OTP), or the like. The computer readable medium may also include any other volatile or non-volatile storage systems. The computer readable medium may be considered computer readable storage medium, for example, or a tangible storage device.

Furthermore, for the method 500 and other processes and methods discussed herein, each block of FIG. 5A may represent circuitry that is wired to perform the specific logical functions of the process.

The method 500 is one example of a method for fitting the hearing prostheses 101, 102 by causing the electrodes in an interaural electrode pair to simultaneously stimulate the user's cochlea. With regard to stimulating the user's cochlea, "simultaneously," as used herein, means the electrodes in an interaural electrode pair stimulate the user's cochlea such that the user perceives a sound in both ears at the same time. Thus, the phrases "simultaneously stimulate," "delivered simultaneously," "simultaneously cause," and the like should not be understood as requiring signals and/or stimuli to be delivered and/or received at exactly the same time. Rather, such phrases should be understood as indicating that there is an overlap between the delivery and/or reception of the signals and/or stimuli that allow the user to perceive a single sound rather separates sounds from the user's left ear and right ear.

How the user of the hearing prostheses 101, 102 perceives a location of the sound depends on how the user's brain "fuses"—or processes—sounds received from the user's left auditory pathway and right auditory pathway. As used herein, the term "auditory pathway" refers to the body parts between the user's outer ear and brain that allow the user to perceive sound. When the brain receives auditory signals from the left auditory pathway and right auditory pathway, the brain processes the sounds together, which assists the user in locating the origin of the sound.

Figure 5B:
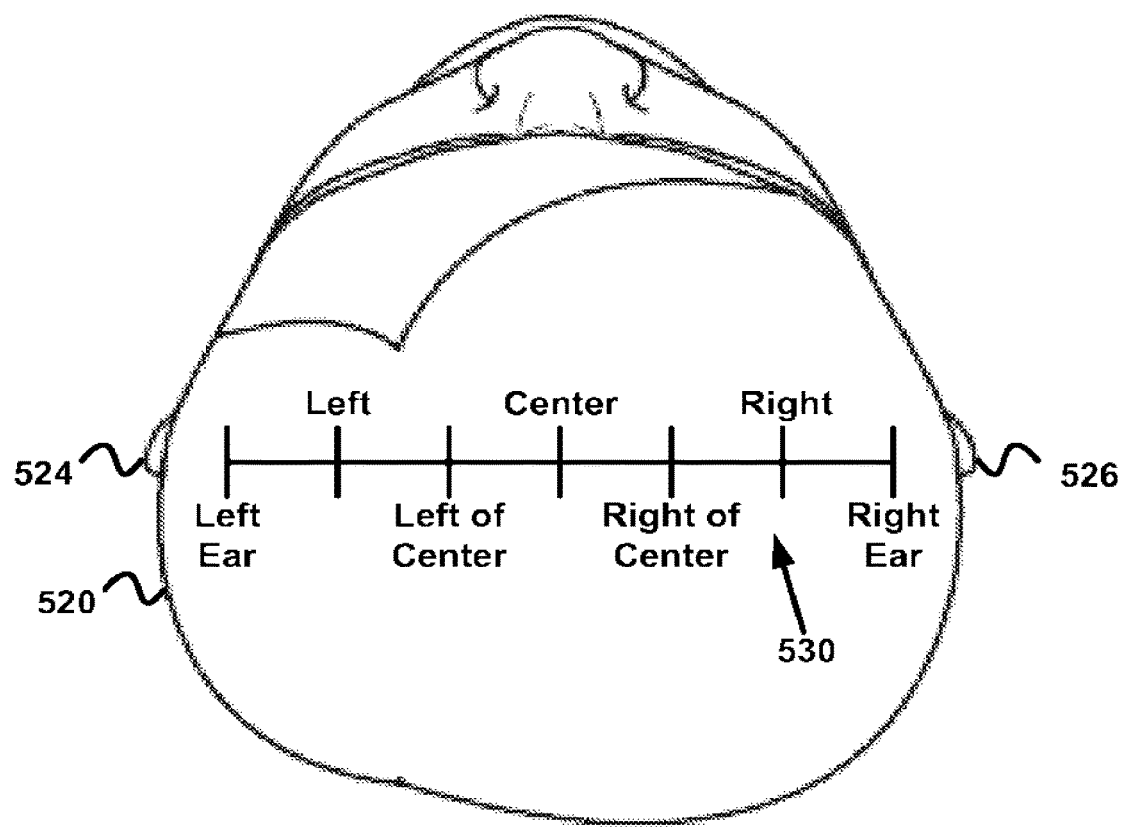
FIG. 5B is an illustration of different perceptual locations of a sound by a user of bilateral hearing prostheses, according to an example.

FIG. 5B illustrates possible perceptual locations of a sound in the head 520 of the user. When the user's brain fuses a sounds received by the left auditory pathway and the right auditory pathway, the user perceives the sound as being between the left ear 524 and the right ear 526, as illustrated by the spectrum 530. When the hearing prostheses 101, 102 are fitted independently, the user may develop a bias toward the ear with less hearing loss. For example, consider a user having greater hearing loss in the user's left auditory pathway than the user's right auditory pathway. Fitting the hearing prostheses 101, 102 independently may cause the user to develop a bias toward the right side of the spectrum 530.

Such biases can cause the user to misperceive the origin of the sound. For instance, if the user perceives a sound as being left of center or left on the spectrum 530 when a person with normal hearing would perceive the sound as being approximately centered, the user will have difficulty identifying the source of the sound. Depending on the situation, the misperception of the origin of a sound may be an annoyance (e.g., the user has difficulty locating a person in a crowd calling the user's name) or a safety risk (the user misidentifies the source of a car horn when crossing a street).

Fitting the hearing prostheses 101, 102 in parallel allows the user to identify potential biases due to different levels of hearing loss in the user's auditory pathways at different frequencies. As described herein, the user can utilize the computing device 106 to simultaneously stimulate interaural electrode pairs. The user can adjust the stimulus currents for one or more electrodes in an interaural electrode pair such that the user perceives a tone as being approximately centered between on the spectrum 530. This allows the user to perceive sounds over a range of frequencies more like a person with normal hearing, allowing the user to more accurately identify the source of a sound in an environment. Additionally, fitting the hearing prostheses 101, 102 in parallel reduces the amount of time taken to fit the hearing prostheses 101, 102 to the user.

Returning to FIG. 5A, the method 500 includes determining a T-Level for each of the electrodes L1-L9, R1-R9 of the hearing prostheses 101, 102, at block 502. The computing device 106 determines the T-Levels for the electrodes L1-L9, R1-R9 individually. To determine the T-Level of the electrode L1, the computing device 106 sends a test signal to the first processing unit 110 that causes the electrode L1 to deliver a stimulus to the user's left cochlea using an initial stimulus current. The first processing unit 110 processes the test signal and sends the stimulation signal to the first implanted unit 112, which causes the electrode L1 to deliver the electrical stimulus to the user's left cochlea using the initial stimulus current.

Upon delivery of the electrical stimulus, the user perceives a tone, the frequency of which depends on the region of the user's left cochlea being stimulated. Based on the user's perception of the tone (e.g., the tone's loudness), the user interacts with an input component of the user interface module 404 to raise or lower the stimulus current of the electrode L1 until the user can barely hear the tone. That is, the user adjusts the stimulus current of the electrode L1 until the user identifies a lowest current at which the user can perceive the tone. In one example, the input component is the fitting interface 440.

Once the user has identified the stimulus current below which the user cannot hear the tone, the computing device 106 determines that the stimulus current is the T-Level for the electrode L1. The computing device 106 repeats this process to determine T-Levels for the remaining electrodes L2-L9 of the first electrode array 114 and the electrodes R1-R9 of the second electrode array 124.

Other procedures for determining the T-Levels of the electrodes L1-L9, R1-R9 are also possible. In one example, the computing device 106 sends a test signal to one of the processing units 110 that causes a group of electrodes to stimulate the user's left cochlea, such as a group of electrodes that includes the electrodes L1-L3. The resulting stimuli cause the user to perceive a multi-tonal sound. The user adjusts the stimulus currents for the group of electrodes until the user identifies the current below which the user cannot perceive the multi-tonal sound. Once the user has identified the stimulus current below which the user cannot hear the tone, the computing device 106 determines that the corresponding stimulus currents are the T-Levels for the electrodes L1-L3. The computing device 106 repeats this process for the remaining electrodes on each of the electrode arrays 114, 124 until the T-Levels are determined for each of the electrodes L1-L9, R1-R9. In subsequent iterations of this process, the group of electrodes may contain more or fewer electrodes than the above-identified group.

In another example, the computing device 106 is configured to determine the T-Levels for a subset of electrodes on an electrode array and to interpolate the T-Levels of the remaining electrodes on the electrode array. For instance, the computing device 106 determines the T-Levels for each of the electrodes L1, L3, L5, L7, and L9. The computing device 106 then interpolates the T-Levels for the electrodes L2, L4, L6, and L8 based on the T-Levels for the electrodes L1, L3, L5, L7, and L9. The computing device 106 repeats the process for the electrodes R1-R9, perhaps by interpolating more or fewer T-Levels.

At block 504, the method 500 includes determining a C-Level for each of the electrodes L1-L9, R1-R9 of the hearing prostheses 101, 102 by stimulating interaural electrode pairs. The computing device 106 is configured to send the test signal to both processing units 110, 120 when determining the C-Levels of interaural electrode pairs. The test signal causes an interaural electrode pair, such as the interaural electrode pair L1 and R1, to simultaneously deliver electrical stimuli to the user's cochlea using an initial maximum stimulus current. The initial maximum stimulus current is a predetermined offset above the T-Level. For instance, if the T-Level is 100 units of current and the offset is 20 units of current, then the initial maximum stimulus current is 120 units of current.

Simultaneous stimulation of the user's cochlea causes the user to perceive a tone in both of the user's ears. In one example, a slight offset exists between a delivery of a stimulus current from the electrode L1 and a delivery of a stimulus current from the electrode R1. The offset may cause the user to incorrectly perceive a perceptual location of the tone on the spectrum 530. To account for the possible offset, the currents of the stimuli delivered by the electrodes L1 and R1 are ramped up to the initial maximum stimulus current. In this example, the computing device 106 sends a series of test signals to the processing units 110, 120 that increase the current of the stimuli delivered by the electrodes L1, R1 from the respective T-Levels to the initial maximum stimulus current.

How the user perceives the tone depends on a number of factors, such as, for instance, the severity of the user's hearing loss in each ear and the placement of electrodes in the user's cochlea. For example, if the user has more severe hearing loss in the user's right ear than the user's left ear, the user may perceive the tone as being located between left or right of the center position on the spectrum 530. In one example, the user perceives the tone as being louder in the one ear than the other.

To account for the differences in interaural hearing loss, the user interacts with the fitting interface 440 to adjust the stimulus currents of the electrodes L1 and R1 until the user perceives the tone as being approximately centered between the user's ears.

The user also interacts with the fitting interface 440 to increase or decrease the stimulus currents of the electrodes L1 and R1 until the user substantially centers the tone between the user's ears and identifies the currents above which the loudness of the tone is too loud. The computing device 106 then determines that the stimulus currents for the electrodes L1 and R1 are the C-Levels for the electrodes L1 and R1, respectively. The computing device 106 repeats this process for determining the C-Levels for additional interaural electrode pairs until the computing device 106 determines the C-Level for each of the electrodes L1-L9, R1-R9.

Other procedures for determining the C-Levels of the electrodes L1-L9 and R1-R9 are also possible. In one example, the computing device 106 sends a test signal to the processing units 110, 120 that causes a group of interaural electrode pairs to stimulate the user's cochlea, such as a group that includes the interaural electrode pairs L1-R1, L2-R2, and L3-R3. When the processing units 110, 120 send the resulting stimulation signals to the implanted units 112, 122, the implanted units 112, 122 cause the electrodes L1-L3 and R1-R3 to simultaneously stimulate the user's cochlea. Consequently, the user perceives a multi-tonal sound. The user adjusts the stimulus currents of the interaural electrode pairs until the user identifies the stimulus currents in which the multi-tonal sound is approximately centered between the user's ears and above which the user perceives the multi-tonal sound as being too loud. The computing device 106 then determines that the stimulus level of each of the electrodes L1-L3, R1-R3 is the electrode's C-Level. The computing device 106 repeats this process for the remaining electrodes on the electrode arrays 114, 124 until the computing device 106 determines the C-Level for each electrode. In subsequent iterations of this process, the group of interaural electrode pairs may contain more or fewer interaural electrode pairs than the above-described group.

In another example, the computing device 106 is configured to determine the C-Level for a subset of interaural electrode pairs and to interpolate the C-Levels of the remaining electrodes based on the determined C-levels. For example, the computing device 106 determines the C-Levels for the interaural electrode pairs L1-R1, L3-R3, L5-R5, L7-R7, and L9-R9. The computing device 106 then interpolates the C-Levels for the remaining electrodes L2, L4, L6, L8, R2, R4, R6, R8 based on the C-Levels of the electrodes L1, L3, L5, L7, L9, R1, R3, R5, R7, and R9.

At block 506, the method 500 includes the computing device 106 receiving a request to fine-tune the mapping curves of the electrodes L1-L9, R1-R9. In one example, the user wishes to fine-tune the mapping curves for one or more interaural electrode pairs to more closely match the user's ability to perceive a sound at one or more frequencies. The user interacts with the user interface module 404, such as a mouse, a keyboard, or a touch screen, to select an option to fine tune one or more mapping curves. For example, the computing device 106 causes the user interface module 404 to display a dialog box on an output component, such as a monitor, display screen, or a touch screen. The dialog box asks the user to select to fine tune one or more mapping curves or to complete the fitting process. The user makes a selection by interacting with an input component of the user interface 404, such as a mouse or a keyboard.

At block 508, the method 500 includes determining whether the user requested to fine tune one or more mapping curves. If the user requested to determine one or more fine-tuned mapping curves, the method 500 includes determining the one or more fine-tuned mapping curves, at block 510. An example method for determining one or more fine-tuned mapping curve is described with respect to FIG. 6 herein.

If the user did not request to determine one or more fine-tuned mapping curves, the method 500 includes the computing device 106 sending the update signals to the processing units 110, 120, at block 512. The computing device 106 sends the first update signal, which includes information indicative of the mapping curve for each of electrodes L1-L9, to the first processing unit 110, and the computing device 106 sends the second update signal, which includes information indicative of the mapping curve for each of electrodes R1-R9, to the second processing unit 120. For each of the electrodes L1-L9, R1-R9, the information indicative of the mapping curve includes at least the electrode's T-Level and C-Level.

If the computing device 106 determined a fine-tuned mapping curve for one or more of the electrodes L1-L9, R1-R9, the computing device 106 includes information of the fine-tuned mapping curve in the update signals sent to processing units 110, 120. For instance, if the computing device 106 determined a fine-tuned mapping curve for the electrode L1, the computing device 106 includes information indicative of the fine-tuned mapping curve in the first update signal. Once the computing device 106 completes the steps of block 512, the method 500 ends.

FIG. 6 is a flow diagram of a method 600 for determining one or more fine-tuned mapping curves. The method 600 is one example of a method that may be employed at block 510 of the method 500. While the fitting system 100, the processing unit 200, and the computing device 400 are described for purposes of illustrating the method 600, it is understood that other devices may be used.

To determine the one or more fine-tuned mapping curves, the computing device 106 "sweeps" through the electrode arrays 114, 124 by causing one or more interaural electrode pairs to sequentially stimulate the user's cochlea. Sweeping through the electrode arrays 114, 124 in this manner allows the user to perceive a series of tones sequentially (e.g., the user perceives a sequence of tones in which the frequency of each tone increases). The user can then identify a frequency at which a tone is not substantially centered on the spectrum 530 and/or a frequency at which the tone does not have the same loudness as other tones during the sweep. The user then interacts with the fitting interface 440 to adjust the stimulus currents of one or more interaural electrode pairs in order to center each tone between the user's ears and to equalize the loudness of the tones. The computing device 106 adjusts the mapping curves of one or more of the electrodes L1-L9, R1-R9 by sweeping uses the adjusted stimulus currents to determine the fine-tuned mapping curves for one or more of the electrodes L1-L9, R1-R9.

At block 602, the method 600 includes the computing device 106 determining a sweep SPL. The sweep SPL is used to determine the stimulus current for each electrode during a sweep of the electrode arrays 114, 124. The sweep SPL is any SPL between $SPL_T$ and $SPL_C$. In one example, the sweep SPL is determined by the following formula:

$$\text{Sweep SPL} = SPL_C - (1-P) \cdot (SPL_C - SPL_T)$$

where P is a percentage in decimal form. Typically, the sweep SPL is greater than $SPL_T$; that is, P is greater than zero. Since the T-Level represents the minimum stimulus current at which the user can perceive a sound at a given frequency, the user may not be able to determine a difference between the perceptual locations and/or a difference in the loudness between two sequential tones. To better ensure the user is able to distinguish differences in the loudness and location of the tones, P is greater than a minimum percentage, such as about 25%, that will result in tones of sufficient loudness that the user can clearly perceive.

At block 604, the method 600 includes the computing device performing a sweep of the interaural electrode pairs. To perform the sweep, the computing device 106 successively sends test signals to the processing unit 110, 120 that cause interaural pairs of electrodes to sequentially stimulate the user's cochlea. For example, the computing device 106 may send a first test signal to the processing units 110, 120 that causes the electrodes L1 and R1 to simultaneously stimulate the user's cochlea. The computing device 106 then sends a second test signal to the processing units 110, 120 that causes the electrodes L2 and R2 to simultaneously stimulate the user's cochlea. The computing device 106 continues sending test signals to the processing units 110, 120 until each interaural electrode pair has stimulated the user's cochlea.

The duration of each test signal is of sufficient length to allow the user to perceive each tone. That is, the computing device 106 does not sweep through the electrode arrays 114, 124 so quickly that the user cannot distinguish each tone. In one example, the duration of each test signal is about 500 msec. In another example, the user can adjust the duration of the test signals.

Additionally, the computing device 106 may send a plurality of test signals to the processing units 110, 120 for each interaural electrode pair that causes the stimulus currents for the interaural electrode pair to ramp up to the stimulus current corresponding to the sweep SPL. Ramping the stimulus currents to the stimulus current corresponding to the sweep SPL provides a control for a potential timing offset in delivery of the stimulus currents, which could affect the user determining the perceptual location of a sound.

In one example, the computing device 106 does not sweep through each electrode on the electrode arrays 114, 124. In this example, the user selects a group of interaural electrode pairs that the computing device uses during the sweep of the electrode arrays. For instance, the computing device 106 sends test signals to the processing units 110, 120 that cause the interaural electrode pairs L1-R1, L3-R3, and L6-R6 to sequentially stimulate the user's cochlea. In another example, the test signals cause groups of interaural electrode pairs to simultaneously stimulate the user's cochlea. For example, the first test signal causes the interaural electrode pairs L1-R1 and L2-R2 to stimulate the user's cochlea, and the second test signal causes the interaural electrode pairs L3-R3 and L4-R4 to stimulate the user's cochlea. In yet another example, the test signals cause more or fewer interaural electrode pairs to simultaneously stimulate the user's cochlea.

At block 606, the method 600 includes the computing device 106 receiving an adjustment to an interaural electrode pairs via the fitting interface 440. If the user identified one or more stimulus currents that require an adjustment during or after the sweep, the user adjusts the stimulus currents of one or more interaural electrode pairs in order to substantially center each tone between the user's ears and to match the loudness of the tones the user perceived during the sweep.

At block 608, the method 600 includes the computing device 106 determining whether an adjustment to a stimulus current was received. If the computing device 106 determines that an adjustment to a stimulus current was received, the method 600 includes returning to block 604 to perform an additional sweep using the adjusted stimulus currents. Otherwise, the method 600 proceeds to block 610.

At block 610, the method 600 includes determining if there are additional sweeps to perform. Typically, the computing device 106 performs sweeps using at least two sweep SPLs. The user may interact with an input component of the user interface 404 to select additional sweep SPLs. Alternatively, the additional sweep SPLs may be predetermined. In another example, the user interacts with user interface module 404 to cause the computing device 106 to perform a single sweep. If the computing device 106 determines that there are additional sweeps to perform, the sweep SPL is set to the next SPL at block 612. The method 600 then includes returning to block 604 to perform an additional sweep of the electrode arrays 114, 124 using the next SPL.

If the computing device 106 determines that the requested sweeps have been performed, the method 600 includes the computing device 106 determining one or more fine-tuned mapping curves, at block 614. For each electrode that delivered a stimulus during the sweep, the computing device 106 determines the fine-tuned mapping curve based on the stimulus currents determined during the sweep(s) of the electrode arrays 114, 124. After the computing device 106 completes the steps of block 614, the method 600 ends.

Figure 7A:
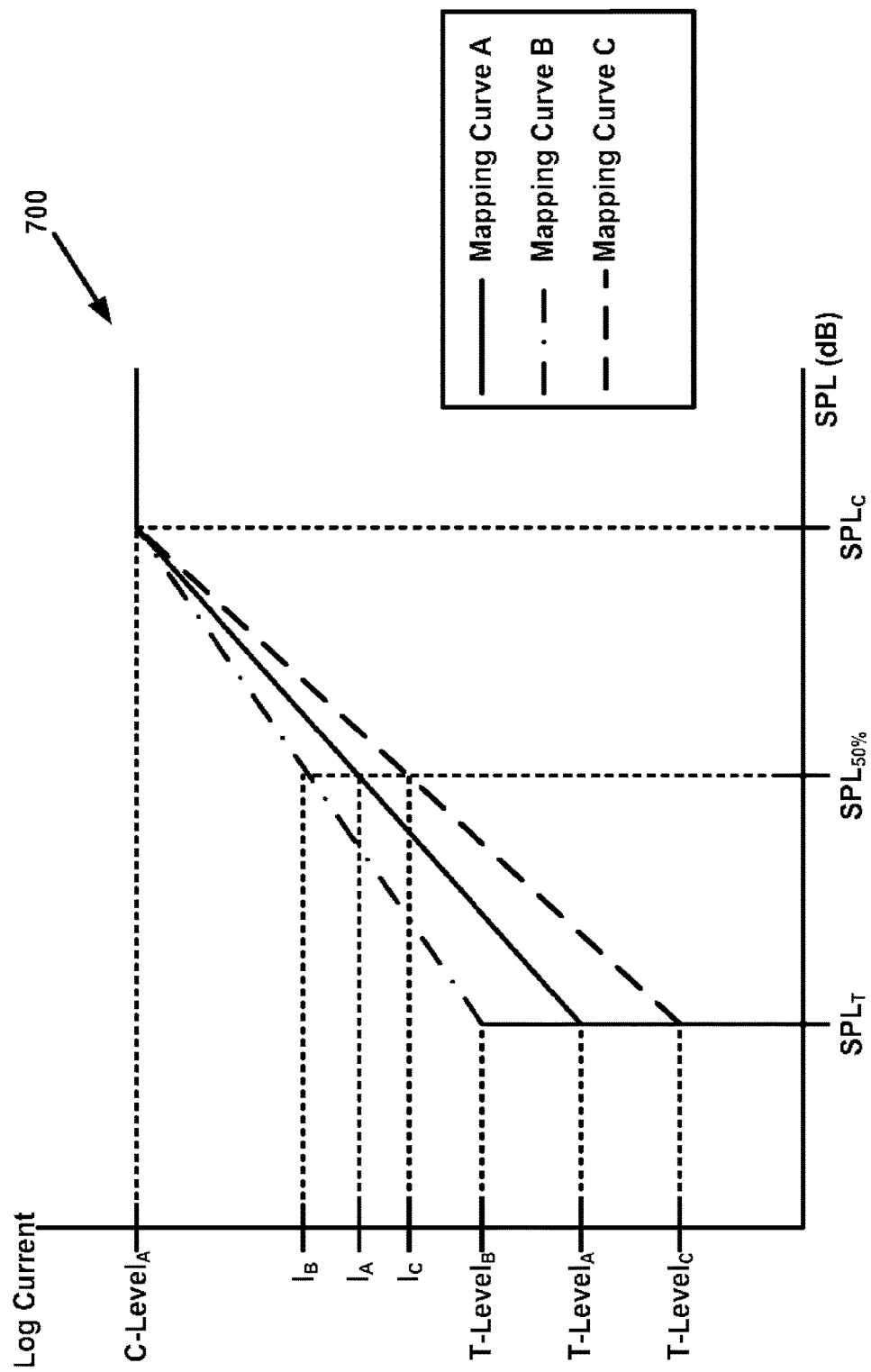
FIGS. 7A-7C are graphs of mapping curves determined using the method depicted in FIG. 6, according to an example.
Figure 7B:
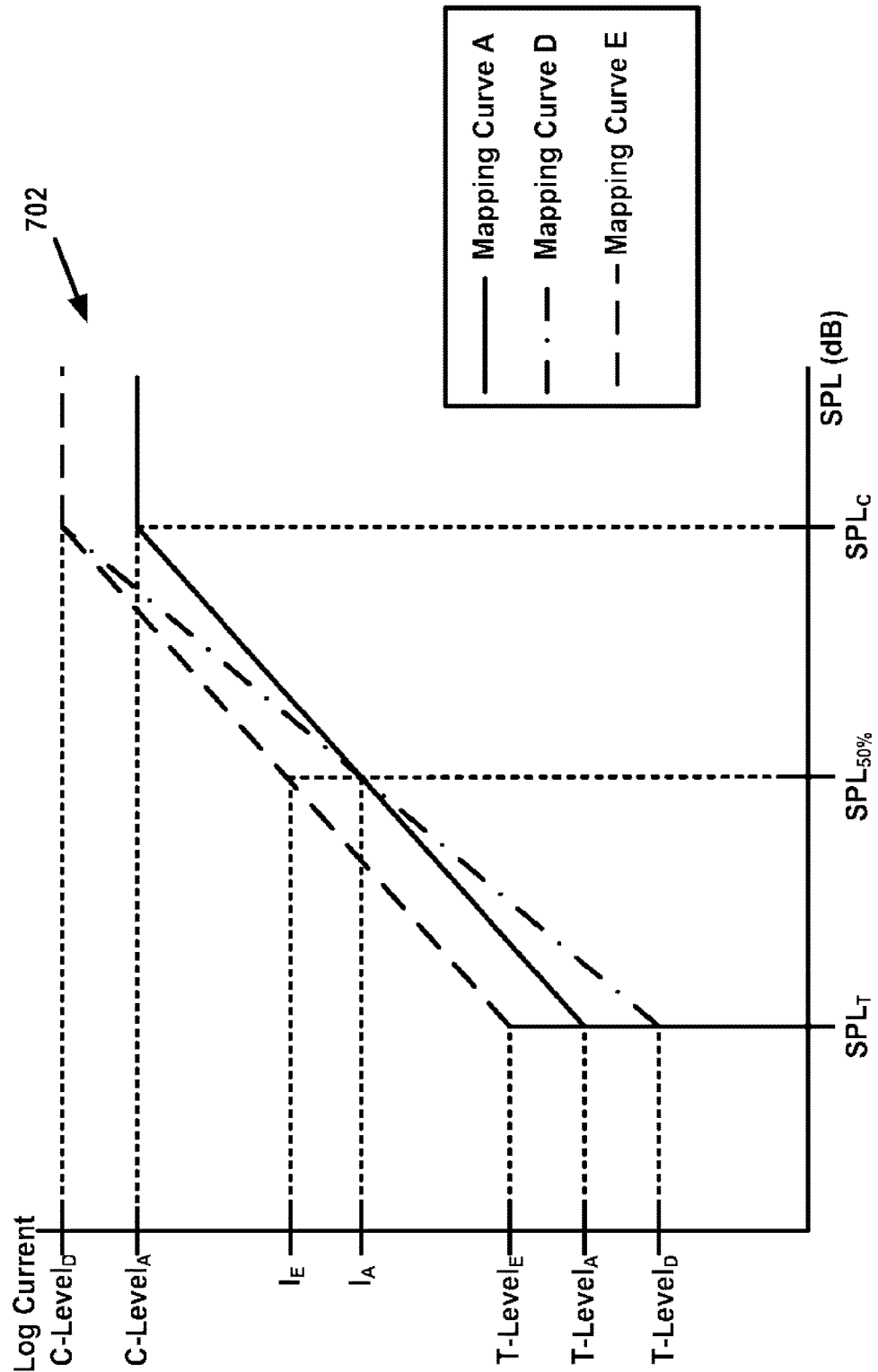
Figure 7C:
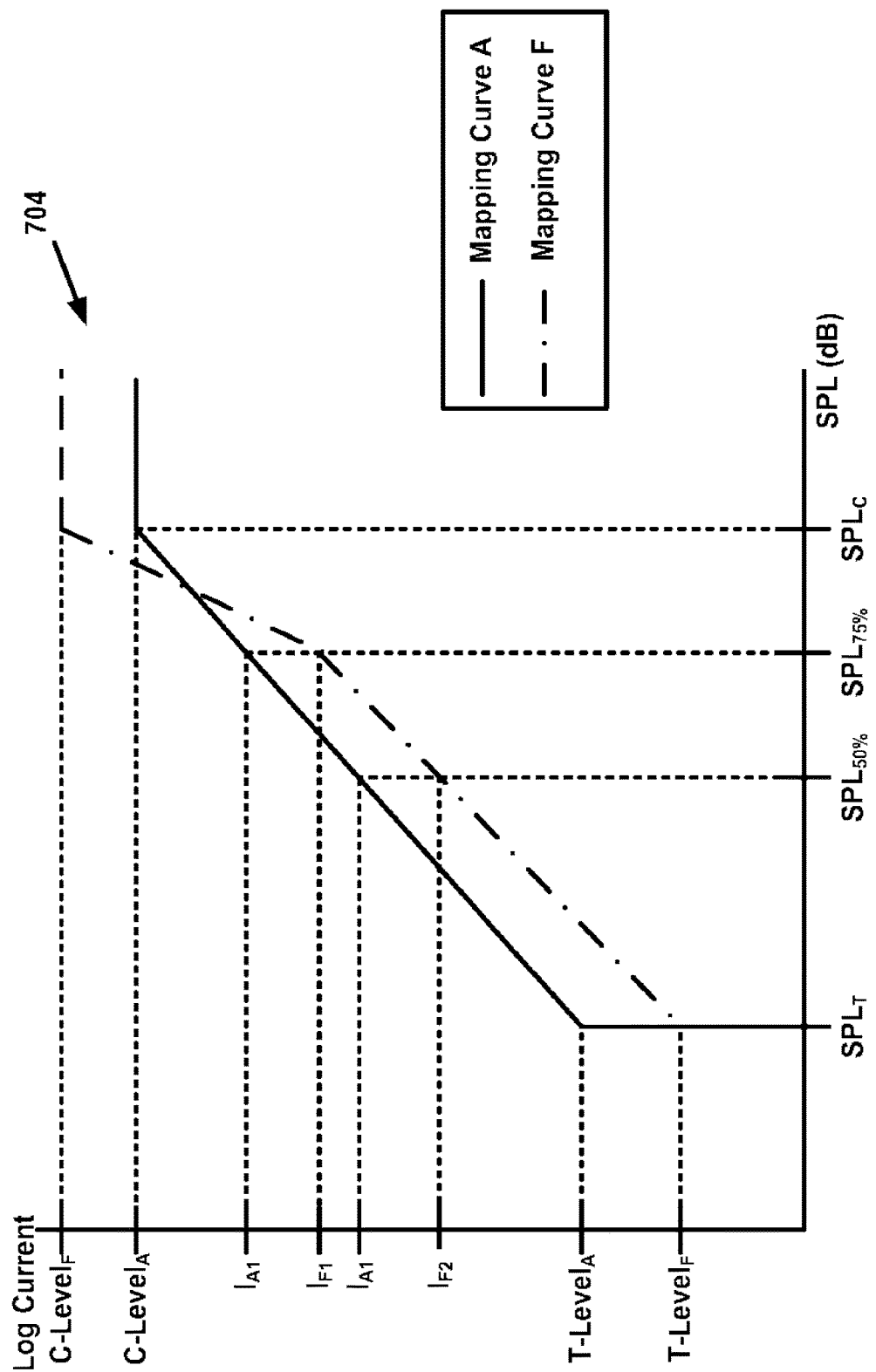

FIGS. 7A-7C illustrate example fine-tuned mapping curves for an electrode determined using the method 600. For illustrative purposes, the electrode L1 depicted in FIG. 1C is used to describe FIGS. 7A-7C.

The mapping curves illustrated in FIGS. 7A-7B are based on two sweeps where P is 50% ($SPL_{50}$%) and 100% ($SPL_C$). In another example, different values of P are used to develop fine-tuned mapping curves. FIG. 7A illustrates a graph 700 of three mapping curves: mapping curve A, mapping curve B, and mapping curve C. Mapping curve A is an initial mapping curve of the electrode L1 based on an initial T-Level (T-Level$_A$) and an initial C-Level (C-Level$_A$). The IA is the stimulus current of the electrode L1 at $SPL_{50}$%. Mapping curve B is a fine-tuned mapping curve determined in response to the user increasing the stimulus current during the sweep at $SPL_{50}$% from IA to $I_B$. Mapping curve C is a fine-tuned mapping curve determined in response to the user decreasing the stimulus current during the sweep at $SPL_{50}$% from $I_A$ to $I_C$.

Mapping curves B-C illustrate how adjustments to the stimulus current at $SPL_{50}$% affect the dynamic range of the electrode. The C-Level for the three mapping curves is the same because the user did not adjust the stimulus currents corresponding to $SPL_C$. Since $I_B$ is greater than $I_A$, the slope of mapping curve B is less than the slope of mapping curve A. As a result, the T-Level for mapping curve B (T-Level$_B$) is greater than the T-Level$_A$. In contrast, since $I_C$ is less than $I_A$, the slope of mapping curve C is greater than the slope of mapping curve A, and the T-Level for mapping curve C (T-Level$_C$) is less than T-Level$_A$.

FIG. 7B illustrates a second graph 702 of three mapping curves: mapping curve A, mapping curve D, and mapping curve E. Mapping curve A is the same as or is substantially similar to mapping curve A as described with respect to FIG. 7A. Mapping curve D is a mapping curve determined in response to the user increasing the stimulus current during the sweep at $SPL_C$ from C-Level$_A$ to C-Level$_D$. Mapping curve E is a mapping curve determined in response to the user increasing the stimulus current during the sweep at $SPL_C$ to C-Level$_D$ and increasing the stimulus current during the sweep at $SPL_{50\%}$ from $I_A$ to $I_E$.

Mapping curves D-E illustrate how adjustments to the stimulus current at $SPL_C$ and/or $SPL_{50\%}$ affect the dynamic range of the electrode. C-Level$_A$ is less than C-Level$_D$, but the stimulus currents at $SPL_{50\%}$ for mapping curve A and mapping curve D is the same. Thus, the slope of mapping curve D is greater than the slope of mapping curve A, and the T-Level for mapping curve D (T-Level$_D$) is less than the T-Level$_A$. For mapping curve E, a difference between $I_E$ and IA is about the same as a difference between C-Level$_D$ and C-Level$_A$. Thus, the slope of mapping curve E is about the same as the slope of mapping curve A, but the T-Level for mapping curve E (T-Level$_E$) is greater than T-Level$_A$.

FIG. 7C illustrates a graph 704 of two mapping curves: mapping curve A and mapping curve F. Mapping curve A is the same as or is substantially similar to mapping curve A as described with respect to FIG. 7A. Mapping curve F is a mapping curve based on three sweeps where P is 50% ($SPL_{50\%}$), 75% ($SPL_{75\%}$), and 100%. Mapping curve F is a mapping curve determined in response to the user increasing the stimulus current during the sweep at $SPL_C$ from to C-Level$_F$, decreasing the stimulus current during the sweep at $SPL_{75\%}$ from $I_{A1}$ to $I_{F1}$, and decreasing the current at $SPL_{50\%}$ from $I_{A2}$ to $I_{F2}$.

Mapping curve F illustrates how adjustments to the stimulus currents at more than two sweep SPLs affects the dynamic range of the electrode. C-Level$_A$ is less than C-Level$_F$, but $I_{A1}$ is greater than $I_{F1}$. Thus, the slope of mapping curve F is greater than the slope of mapping curve A between $SPL_{75\%}$ and $SPL_C$. The change in the stimulus current at $SPL_{50\%}$ from $I_{A2}$ to $I_{F2}$ causes a change in the slope of mapping curve F between $SPL_T$ and $SPL_{50\%}$. The slope of mapping curve F between $SPL_{75\%}$ and $SPL_C$ is greater than the slope of mapping curve F between $SPL_T$ and $SPL_{50\%}$. Since the slope of mapping curve A is less than the slope of mapping curve F between $SPL_T$ and $SPL_{75\%}$, T-Level$_A$ is greater than T-Level$_F$.

As the graphs 700, 702, and 704 illustrate, fine-tuning the mapping curve of an electrode may result in an adjustment to the T-Level of the electrode. Since the T-Level is the level below which the user is unable to perceive a sound and is determined for each electrode individually, fine-tuning the dynamic range may result in a more accurate setting for the T-Level. Additionally, fine-tuning the mapping curve results in a more accurate logarithmic relationship between the SPL of an incoming sound and a resulting stimulus current.

4. CONCLUSION

While the descriptions of methods 500 and 600 are based on the fitting system 100 including two cochlear implants, the computing device 106 may employ the methods 500 and/or 600 to fit bilateral hearing prostheses that are not cochlear implants. For instance, if the hearing prostheses 101, 102 are bone conduction devices, the implanted units 112, 122 include a left transducer and a right transducer, respectively, instead of the electrode arrays 114, 124. In this example, the implanted units 112, 122 use the transducers to cause vibrations on the user skull capable of stimulating the user's cochlea. The computing device 106 uses the method 500 to determine a minimum amplitude (e.g., T-Levels) of the vibrations for each transducer at a frequency and maximum amplitude (e.g., C-Levels) of the vibrations for each transducer at a frequency of the vibrations applied by simultaneously applying vibrations to the user's skull using the left and right transducers.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A computing device, comprising:
a user interface configured to receive an indication of an adjustment to at least one of a first stimulus and a second stimulus delivered by a first hearing prosthesis and a second hearing prosthesis, respectively, to a recipient;
an interface module configured to connect the computing device to the first and second hearing prostheses; and
a processor configured to:
receive an input signal from the user interface that includes information indicative of the adjustment to the at least one of the first stimulus and the second stimulus;
determine a modification of the first stimulus and the second stimulus based on the adjustment;
send a first signal to the first hearing prosthesis that includes information indicative of a modified first stimulus; and
send a second signal to the second hearing prosthesis that includes information indicative of a modified second stimulus, wherein the first signal causes the first hearing prosthesis to deliver the modified first stimulus to the recipient at about a same time as the second signal causes the second hearing prosthesis to deliver the modified second stimulus to the recipient.

2. The computing device of claim 1, wherein the user interface includes a first input interface, a second input interface, a third input interface, and a fourth input interface.

3. The computing device of claim 2, wherein an interaction with the first input interface increases the first stimulus and increases the second stimulus.

4. The computing device of claim 2, wherein an interaction with the second input interface decreases the first stimulus and decreases the second stimulus.

5. The computing device of claim 2, wherein an interaction with the third input interface increase the first stimulus and decreases the second stimulus.

6. The computing device of claim 2, wherein an interaction with the fourth input interface decreases the first stimulus and increases the second stimulus.

7. The computing device of claim 1, wherein the user interface includes an external hardware component, and wherein the first input interface, the second input interface, the third input interface, and the fourth input interface are included on the external hardware component.

8. The computing device of claim 1, wherein the user interface includes a display device, and wherein the first input interface, the second input interface, the third input interface, and the fourth input interface are displayed on the display device.

9. The computing device of claim 1, wherein the first and second stimulus are delivered to first and second ears, respectively, of the recipient to evoke perception of first and second sounds by the recipient, and wherein the information indicative of the adjustment to the at least one of the first stimulus and the second stimulus comprises an indication of a difference between the first sound and the second sound as perceived by the recipient.

10. The computing device of claim 9, wherein the one or more processors are configured to:
determine, based on the indication, an adjustment to either the first or the second stimulation signal delivered to the recipient, and
apply the adjustment to a mapping curve that includes information indicative of a plurality of different stimuli corresponding to a plurality of different sound pressure levels.

11. The computing device of claim 10, wherein at least the first hearing prosthesis comprises a cochlear implant configured to deliver the first stimulus via one or more electrodes, and wherein to apply the adjustment to a mapping curve, the one or more processors are configured to:
apply the adjustment to a mapping curve of at least one of the one or more electrodes, wherein the mapping curve includes information indicative of a plurality of stimulus currents corresponding to a plurality of sound pressure levels.

12. The computing device of claim 11, wherein the mapping curve of the at least one electrode represents a relationship between input sound pressure levels and stimulus currents of the at least one electrode that is substantially logarithmic between a threshold sound pressure level and a maximum sound pressure level, wherein the threshold sound pressure level corresponds to a stimulus current for the at least one electrode below which the recipient is unable to perceive a sound, and wherein the maximum sound pressure level is a saturation sound pressure level for the at least one electrode.

13. The computing device of claim 12, wherein the stimulus current corresponds to a sweep sound pressure level on the mapping curve.

14. The computing device of claim 13, wherein the sweep sound pressure level is greater than the threshold sound pressure level, and the sweep sound pressure level is less than or equal to the maximum sound pressure level.

15. A method, comprising:
receiving an indication of an adjustment to at least one of a first stimulus and a second stimulus delivered by a first hearing prosthesis and a second hearing prosthesis, respectively, to a recipient;
determining a modification of the first stimulus and the second stimulus based on the adjustment;
sending a first signal to the first hearing prosthesis that includes information indicative of a modified first stimulus; and
sending a second signal to the second hearing prosthesis that includes information indicative of a modified second stimulus, wherein the first signal causes the first hearing prosthesis to deliver the modified first stimulus to the recipient at about a same time as the second signal causes the second hearing prosthesis to deliver the modified second stimulus to the recipient.

16. The method claim 15, wherein the first and second stimulus are delivered to first and second ears, respectively, of the recipient to evoke perception of first and second sounds by the recipient, and wherein the information indicative of the adjustment to the at least one of the first stimulus and the second stimulus comprises an indication of a difference between the first sound and the second sound as perceived by the recipient.

17. The method of claim 16, further comprising:
determining, based on the indication, an adjustment to either the first or the second stimulation signal delivered to the recipient, and applying the adjustment to a mapping curve that includes information indicative of a plurality of different stimuli corresponding to a plurality of different sound pressure levels.

18. The method of claim 17, wherein at least the first hearing prosthesis is a cochlear implant configured to deliver the first stimulus via one or more electrodes, and wherein to apply the adjustment to a mapping curve, the one or more processors are configured to:

apply the adjustment to a mapping curve of at least one of the one or more electrodes, wherein the mapping curve includes information indicative of a plurality of stimulus currents corresponding to a plurality of sound pressure levels.

19. The method of claim 18, wherein the mapping curve of the at least one electrode represents a relationship between input sound pressure levels and stimulus currents of the at least one electrode that is substantially logarithmic between a threshold sound pressure level and a maximum sound pressure level, wherein the threshold sound pressure level corresponds to a stimulus current for the at least one electrode below which the recipient is unable to perceive a sound, and wherein the maximum sound pressure level is a saturation sound pressure level for the at least one electrode.

\* \* \* \* \*